United States Patent
Polluks et al.

(10) Patent No.: US 12,042,128 B2
(45) Date of Patent: Jul. 23, 2024

(54) ENDOSCOPE DEVICE FOR A FLEXIBLE ENDOSCOPE, AND METHOD FOR PRODUCING AN ENDOSCOPE DEVICE

(71) Applicant: KARL STORZ SE & CO. KG, Tuttlingen (DE)

(72) Inventors: Indrek-Toomas Polluks, Rakvere (EE); Craig Fitzpatrick, Tempe, AZ (US)

(73) Assignee: KARL STORZ SE & CO. KG, Tuttlingen (DE)

( * ) Notice: Subject to any disclaimer, the term of this patent is extended or adjusted under 35 U.S.C. 154(b) by 339 days.

(21) Appl. No.: 17/105,403

(22) Filed: Nov. 25, 2020

(65) Prior Publication Data

US 2021/0153728 A1  May 27, 2021

Related U.S. Application Data (60) Provisional application No. 62/940,650, filed on Nov. 26, 2019.

(51) Int. Cl.
*A61B 1/00* (2006.01)
*A61B 1/012* (2006.01)
(Continued)

(52) U.S. Cl.
CPC .......... *A61B 1/012* (2013.01); *A61B 1/0008* (2013.01); *A61B 1/018* (2013.01); *A61L 29/041* (2013.01);
(Continued)

(58) Field of Classification Search
CPC ....... A61B 1/012; A61B 1/0008; A61B 1/018; A61B 1/0011; A61B 1/0055; A61B 1/05;
(Continued)

(56) References Cited

U.S. PATENT DOCUMENTS

| | | | | |
|---|---|---|---|---|
| 5,620,408 A | * | 4/1997 | Vennes | A61B 1/273 128/207.14 |
| 5,789,047 A | * | 8/1998 | Sasaki | A61B 1/05 428/36.5 |

(Continued)

FOREIGN PATENT DOCUMENTS

DE    10122203 A1    1/2002

OTHER PUBLICATIONS

European Office Action, Application No. EP 20 209 721.8, dated Feb. 22, 2023.
(Continued)

*Primary Examiner* — Timothy J Neal
(74) *Attorney, Agent, or Firm* — Honigman LLP (57) ABSTRACT

A tubular working channel sheath that includes a working channel, a first sheath layer that defines the working channel and includes at least one plastic material. The first sheath layer has a constant layer thickness along an entire length of the working channel. The tubular working channel sheath includes a second sheath layer that includes at least one further plastic material different than the plastic material of the one sheath layer. The second sheath layer has a tapered layer thickness along a length of the working channel, and the tapered layer thickness tapers between a proximal end and a distal end of the working channel.

20 Claims, 3 Drawing Sheets

(51) Int. Cl.
*A61B 1/018* (2006.01)
*A61L 29/04* (2006.01)
*A61L 29/14* (2006.01)
*A61M 25/00* (2006.01)

(52) U.S. Cl.
CPC .... *A61L 29/146* (2013.01); *A61M 2025/0035* (2013.01)

(58) Field of Classification Search
CPC ................ A61L 29/041; A61L 29/146; A61M 2025/0035
See application file for complete search history.

(56) References Cited

U.S. PATENT DOCUMENTS

| | | | | |
|---|---|---|---|---|
| 5,885,209 | A * | 3/1999 | Green | A61B 1/018 600/153 |
| 6,562,021 | B1 * | 5/2003 | Derbin | A61M 25/0045 606/7 |
| 2003/0220545 | A1 * | 11/2003 | Ouchi | A61B 1/018 600/166 |
| 2004/0077927 | A1 * | 4/2004 | Ouchi | A61B 1/018 600/123 |
| 2004/0106853 | A1 * | 6/2004 | Moriyama | A61B 1/0055 348/E7.086 |
| 2009/0030400 | A1 * | 1/2009 | Bose | A61M 25/0023 604/528 |
| 2009/0112066 | A1 | 4/2009 | Yago et al. | |
| 2010/0075075 | A1 | 3/2010 | Takahashi | |
| 2010/0201029 | A1 * | 8/2010 | Yago | B29C 48/34 264/260 |
| 2010/0256445 | A1 * | 10/2010 | Fitzpatrick | A61B 1/00071 600/101 |
| 2011/0220270 | A1 * | 9/2011 | Koori | B29C 48/919 156/144 |
| 2016/0106309 | A1 * | 4/2016 | Begg | A61B 1/313 600/160 |
| 2016/0331873 | A1 * | 11/2016 | Dohse | C08G 63/08 |
| 2017/0028167 | A1 * | 2/2017 | Welch | A61M 25/005 |
| 2017/0191586 | A1 * | 7/2017 | Nadeau | B32B 27/306 |
| 2018/0085181 | A1 * | 3/2018 | Kärcher | A61B 17/29 |
| 2018/0289925 | A1 * | 10/2018 | Palmer | A61M 25/0045 |
| 2018/0333044 | A1 * | 11/2018 | Jenkins | A61B 1/00128 |
| 2019/0133423 | A1 * | 5/2019 | Birnkrant | A61B 1/04 |
| 2020/0129048 | A1 * | 4/2020 | Hamm | A61B 1/00066 |

OTHER PUBLICATIONS

Extended European Search Report (EESR), Application No. EP 20 209 721.8, dated Apr. 29, 2023.

* cited by examiner

ENDOSCOPE DEVICE FOR A FLEXIBLE ENDOSCOPE, AND METHOD FOR PRODUCING AN ENDOSCOPE DEVICE

CROSS REFERENCE TO RELATED APPLICATIONS

This application claims priority to Provisional U.S. Patent Application No. 62/940,650, filed Nov. 26, 2019, and entitled, "Endoskopvorrichtung für ein flexibles Endoskop and Verfahren zu deren Herstellung," and is incorporated herein by reference.

FIELD OF THE INVENTION

The invention relates to endoscopes, and, in particular, endoscopic devices comprising one or more working channels. The invention also relates to methods for producing an endoscopic devices with improved working channels.

BACKGROUND OF THE INVENTION

Endoscopes for medical or non-medical applications usually comprise an elongate shaft configured for being introduced into an internal cavity of a human or animal body or another object to be examined. The shaft may be rigid, semi-flexible, or flexible. Typically, the endoscope has a handle attached to a proximal (i.e. close to a user) end section of the shaft. In a distal (i.e. distant from a user) end section of the shaft an objective lens system is arranged for generating an image of an object field in the cavity of the body or object. In video endoscopes, which also are denoted electronic endoscopes, the generated endoscopic image is picked up by an electronic image sensor. The image sensor is usually arranged in the distal end section of the shaft having its sensor plane in an image plane of the objective lens system The collected image data is then transmitted electronically through the shaft and ultimately to a display device and/or an image processing unit to display the endoscopic image to the user. Such video endoscopes are commonly denoted chip-on-the-tip (COTT) endoscopes. Reusable medical endoscopes require cleaning and sterilization after each use. In most cases reusable medical endoscopes are subjected to an autoclave process including exposure to high temperature and pressurized steam.

Endoscope devices known in the art commonly have one or more working channels, and this working channel usually comprises an internal tubular sheath that defines the volume of the working channel. One or more surgical instruments can made to pass through the working channel.

An "endoscope device" should be understood in particular to mean a constituent part, preferably a functional constituent part, of an endoscope, in particular a subassembly and/or a structural component and/or a functional component of an endoscope. Alternatively, the endoscope device can completely embody an endoscope. The expression "at least largely" should be understood to mean in particular at least 55%, preferably at least 65%, preferably at least 75%, particularly preferably at least 85%, and very particularly preferably at least 95%, or advantageously completely, specifically in relation to a volume and/or mass of an object, in particular. In particular, "configured" should be understood to mean specifically programmed, provided, designed and/or equipped. An object being configured for a specific function should be understood to mean in particular that the object satisfies or carries out this specific function in at least one application state or operational state.

The working channel, as described above, is designed as an elongate component, or negative space, and is suitable for receiving a surgical instrument therein and/or for transporting liquids or gases therethrough. An "elongate component" should be understood in particular to mean a component whose principal extent is greater than an extent of the component at least substantially perpendicular to the principal extent, commonly by a factor of at least 10. A "direction of principal extent" of a component should be understood in particular to mean a direction that extends parallel to a longest edge of a smallest imagined cuboid that just still completely surrounds the component. Here, "at least substantially parallel" should be understood in particular to mean an orientation of a direction relative to a reference direction, in particular in a plane, wherein the direction and the reference direction encompass an angle of 0°, and in general has a deviation of less than 8°, or more advantageously, of less than 5° or even less than 2°. Here, "at least substantially perpendicular" should be understood in particular to mean an orientation of a direction relative to a reference direction, in particular in a plane, wherein the direction and the reference direction encompass an angle of 90°, and in general with maximum deviation of less than 8°, advantageously of less than 5° and most desirably of less than 2°. A "principal extent" of the object should be understood in particular to mean an extent of an object that extends along a longest edge of a smallest imagined cuboid that just still completely surrounds the object.

BRIEF DESCRIPTION OF THE INVENTION

The object of the invention is to enable one or more improved working channels in an endoscopic device. The invention is particularly advantageous to endoscopes with flexible working channels.

The invention is particularly relevant to an endoscope device for an endoscope, in particular a flexible endoscope, with at least one working channel. The working channel has a tubular working channel sheath that delimits a working channel inner volume of the working channel. The working channel sheath having a first sheath layer which comprises at least one plastic material, and having at least one further sheath layer which comprises at least one further plastic material, which is different than the plastic material of the first sheath layer. The further sheath layer surrounds the first sheath layer along the principal extent of the working channel length.

It is preferred that the first sheath layer has a constant layer thickness along the principal extent of the working channel, and that the further sheath layer has a variable layer thickness in portions along the principal extent of the working channel. Through variation of the layer thickness, an arrangement of the working channel, in particular inside an endoscope shaft and/or at an endoscope tip, can be improved. Moreover, the stability of the working channel can also be improved.

The working channel sheath has, in some embodiments, has an particular an internal diameter that measures between 0.5 mm and 2 mm, and at most 12 mm. Preferred embodiments have an internal diameter of between 2 and 3 mm. The first sheath layer has in particular a layer thickness that measures at least 1.5%, preferably at least 2% and particularly preferably at least 3% and/or at most 10%, preferably at most 7% and particularly preferably at most 4% of the internal diameter.

Since a layer thickness of the further sheath layer is variable in portions along the principal extent of the working channel, the further sheath layer has in one portion in particular a layer thickness corresponding to at least 5%, preferably at least 6% and particularly preferably at least 10% and/or at most 15%, preferably at most 13% and particularly preferably at most 11% of the internal diameter.

In the further portion of the working channel sheath, the further sheath layer can have a layer thickness which, in relation to the layer thickness in the first portion, is reduced by at least 10%, preferably at least 25%, particularly preferably at least 40% or more than 50%.

Alternatively, or in addition, in a further portion of the working channel sheath, the further sheath layer can have a layer thickness of at least 0.1%, preferably at least 0.14% and particularly preferably at least 0.18% and/or at most 0.28%, preferably at most 0.24% and particularly preferably at most 0.2% of the internal diameter. The installation space in the distal end portion of endoscopes, which receives various further components such as image sensors, lighting units or parts of the endoscope shaft, may be so limited such that a very great reduction of the thickness of the further sheath layer in some portions of the working channel sheath is useful in order to create further space to facilitate the positioning of these elements within the shaft.

The working channel is flexible in many embodiments of the invention. The first sheath layer and the further sheath layer extend in particular at least substantially parallel along the principal extent. The first sheath layer and the further sheath layer are in particular arranged coaxially. The further sheath layer surrounds the first sheath layer in particular along a circumference of the working channel sheath, at least partly, preferably at least largely, and particularly preferably completely. The first sheath layer and the further sheath layer form the working channel sheath at least partly, preferably at least largely, and particularly preferably completely. The first plastic material forms the first sheath layer in particular at least partly, preferably at least largely, and particularly preferably completely. In other words, the one sheath layer can be free of a further plastic. Moreover, the further sheath layer is in particular formed from the further plastic material in particular at least partly, preferably at least largely, and particularly preferably completely. In other words, the further sheath layer can be free of an additional plastic. Particularly since the first plastic material and the further plastic material are different from each other, these together form at least partly a composite material, from which the working channel sheath is at least partly formed. Preferably, the plastic material and the further plastic material are connected to each other by cohesive bonding and/or by form-fit engagement.

Through the formation of the sheath layers from the plastic materials as described above, it is possible in particular to create a working channel which has a particularly small diameter and small wall thickness and which is suitable for endoscope devices and endoscopes of very small diameter.

In order to reduce the diameter further, the layer thickness of the further sheath layer may be decreased in portions along the principal extent of the working channel. Preferably, the layer thickness of the further sheath layer decreases in portions along the principal extent of the working channel in the distal direction. In particular, a first portion of the working channel sheath is a proximal portion, and a further portion of the working channel sheath is a distal portion. Moreover, the working channel sheath can have an intermediate portion, which is arranged between the first portion and the further portion. Preferably, the in particular greater layer thickness of the first portion merges continuously inside the intermediate portion into the in particular smaller layer thickness of the further portion. The intermediate portion can have a length of a few millimeters, preferably less than 5 mm. The first sheath layer can have a layer thickness in the first portion and in the further portion as described above.

It is further proposed that the working channel sheath, at least in some portions, is free of the further sheath layer. It is thus possible to achieve a particularly compact design of the working channel sheath. For example, the further portion could be free of the second sheath layer. In other words, in the further portion, a layer thickness of the further sheath layer could have the value zero, having tapered off completely in thickness, for example, in the intermediate portion of the working channel sheath.

The distal portion may be a distal end portion of the working channel sheath. Preferably, this distal end portion is free of the further sheath layer. Assembly can advantageously be further simplified, and a diameter of the working channel can be made smaller, in some embodiments, in the distal region.

The first sheath layer and the further sheath layer can be arranged next to each other. It is further proposed that the first sheath layer and the further sheath layer lie on each other. It is thereby advantageously possible to create a particularly stable working channel sheath.

It is proposed that the first sheath layer and the further sheath layer are connected to each other by cohesive bonding and/or form-fit engagement. It is advantageously possible to form a composite material from the first plastic material and the further plastic material of the first sheath layer and of the further sheath layer, for example using pressure and heat. Delamination, i.e. a separation of the two layers from each other, during bending of the working channel can thus be prevented. Working channels in flexible endoscopes are often exposed to bending with a small bending radius, and thus delamination can be a concern, which is obviated by some of the embodiments of the present invention.

The first sheath layer usually forms an inner face of the working channel sheath, and the further sheath layer forms an outer face of the working channel sheath. It is thus advantageously possible to make available a homogeneous inner face, which is largely unimpaired by any design of a further sheath layer stabilizing the first sheath layer.

It is further proposed that an internal diameter of the working channel sheath is constant or at least substantially constant along the principal extent of the working channel. It is thereby possible to ensure that a surgical instrument arranged in the working channel volume delimited by the working channel sheath can be arranged along the entire principal extent of the working channel and/or can be guided therethrough without being damaged or getting stuck. The working channel can nonetheless have bends or branches.

It is further proposed that an external diameter of the working channel sheath is variable along the principal extent of the working channel. This in particular permits individual adaptation of the working channel sheath to an installation space inside an endoscope shaft.

In various embodiments, the external diameter of the first portion of the working channel sheath may correspond to in particular at least 110%, preferably at least 115% and particularly preferably at least 120% and/or at most 145%, preferably at most 140% and particularly preferably at most 135% of the internal diameter. In the further portion of the working channel sheath, the latter has an external diameter corresponding to at least 101%, preferably at least 106% and particularly preferably at least 110% and/or at most 138%, preferably at most 133% and particularly preferably at most 120% of the internal diameter.

While any appropriate plastic material may be used, in preferred embodiments it is particularly advantageous that at least one of the plastic materials is polytetrafluoroethylene (PTFE). The stability can thus advantageously be improved, wherein preferably at the same time a corresponding flexibility of the working channel sheath can be achieved. In particular, the plastic of the first sheath layer can be polytetrafluoroethylene.

Alternatively, or in addition, one of the plastic materials can be or comprise polyether ether ketone (PEEK) or another thermoplastic.

It is further proposed that the first plastic material of the first sheath layer is PTFE. Moreover, the further plastic of the further sheath layer may comprise or consist of polytetrafluoroethylene, although it differs from the first plastic in that it is expanded (expanded polytetra-fluoroethylene (ePTFE)). PTFE is inert and has a low coefficient of friction, such that fluids or instruments can be transported or moved particularly easily within the working channel. Moreover, the material can be subjected to high temperatures, for example when the working channel is cleaned in an autoclave. In relation to PTFE, expanded PTFE in turn has improved strength characteristics. It is suitable for being heated and compressed in order to vary the thickness of the further sheath layer. The combination of the sheath layers made of PTFE and ePTFE creates a particularly flexible and at the same time stable working channel, the diameter or sheath thickness of which can be varied according to requirements and adapted to the design of the instrument.

It is moreover proposed that the plastic material of the sheath layer is designed free of pores, and thus, the leak-tightness of the working channel sheath can advantageously be improved. The plastic material of the sheath layer preferably has a density of less than 3 g/cm3. This is particularly the case with PTFE. The density of the plastic material of the sheath layer is in particular constant along the principal extent of the working channel.

It is further proposed that the further sheath layer has a further plastic material, which has pores. A flexibility and at the same time the stability of the working channel sheath can advantageously be improved.

It is further proposed that the further sheath layer has a further plastic material with pores and, in the region of a decreasing layer thickness, is designed free of pores. When ePTFE is used as the further plastic material, the latter has pores, although in the region of a reduced or decreasing layer thickness it can be free of pores, for example when it has been heated and compressed in this region in order to vary the layer thickness. As has already been described, this can be the case in at least one further portion of the working channel. This portion, having an outer surface without pores, is particularly suitable for being glued or otherwise cohesively bonded to other components of the endoscope device or of the endoscope.

The plastic material of the further sheath layer preferably has a density of less than 3 g/cm3, and more preferably less than 2 g/cm3. The plastic material has in particular a density of at most 1.7 g/cm3 and particularly preferably at most 1.6 g/cm3. Moreover, the plastic material of the further sheath layer can have in particular a density of at least 0.6 g/cm3, preferably at least 0.8 g/cm3 and particularly preferably at least 1.0 g/cm3. The plastic material may have a variable density in portions along a principal extent of the working channel. The density of the plastic material of the sheath layer varies in particular constantly along the principal extent of the working channel. Preferably, a variation of the density of the plastic material is coupled to the variation of the layer thickness of the further sheath layer. The density can be increased in particular in the region of the further portion, for example if the further plastic material has been compressed in order to reduce the thickness of the further sheath layer.

The density of the plastic material of the further sheath layer is in particular less than that of the plastic material of the first sheath layer.

It is moreover proposed that the endoscope device comprises at least one distal endoscope tip, to which the working channel is connected by cohesive bonding and/or by form-fit engagement. The working channel can be glued, in particular in a distal portion, to the endoscope tip. In this way, the working channel is fixed in its position relative to the endoscope and yet remains flexible.

In a further aspect of the invention, an endoscope having at least one such endoscope device is proposed. The production and the useful life of the endoscope can thereby be improved. In particular, the endoscope can comprise at least two or more such endoscope devices.

In a further aspect of the invention, a method is proposed for producing an endoscope device, the endoscope device designed, as described above, for a flexible endoscope in which method a working channel is formed. The working channel has a tubular working channel sheath that delimits or encloses a working channel volume of the working channel, and that has at least one first sheath layer which comprises at least one plastic material, and that has at least one further sheath layer which comprises at least one further plastic material, which is different than the plastic material of the sheath layer, wherein, in at least one method step, a layer thickness of the sheath layer is maintained constant along the principal extent of the working channel, and a layer thickness of the further sheath layer is varied in portions along the principal extent of the working channel. The production and the useful life of the endoscope can thereby be improved. Preferably, the layer thickness is varied at least in one portion by means of the sheath layer being heated and/or subjected to pressure and thus compressed. In this way, in particular, the plastic material of the further sheath layer can be at least partially varied, removed or converted into the plastic material of the sheath layer. For example, as has already been described for the endoscope device, the thickness of the further sheath layer is varied, and in particular reduced, in a distal portion of the working channel sheath.

BRIEF DESCRIPTION OF THE DRAWINGS

Further advantages will become clear from the following description of the drawings. The drawings illustrate two exemplary embodiments of the invention. The drawings, the description and the claims contain numerous features in combination. A person skilled in the art will expediently also consider the features individually and combine them to form meaningful further combinations. The detailed description given herein, and the accompanying drawings, are given by way of illustration only, and thus are not limitative of the present invention.

DETAILED DESCRIPTION OF THE INVENTION

Figure 1:
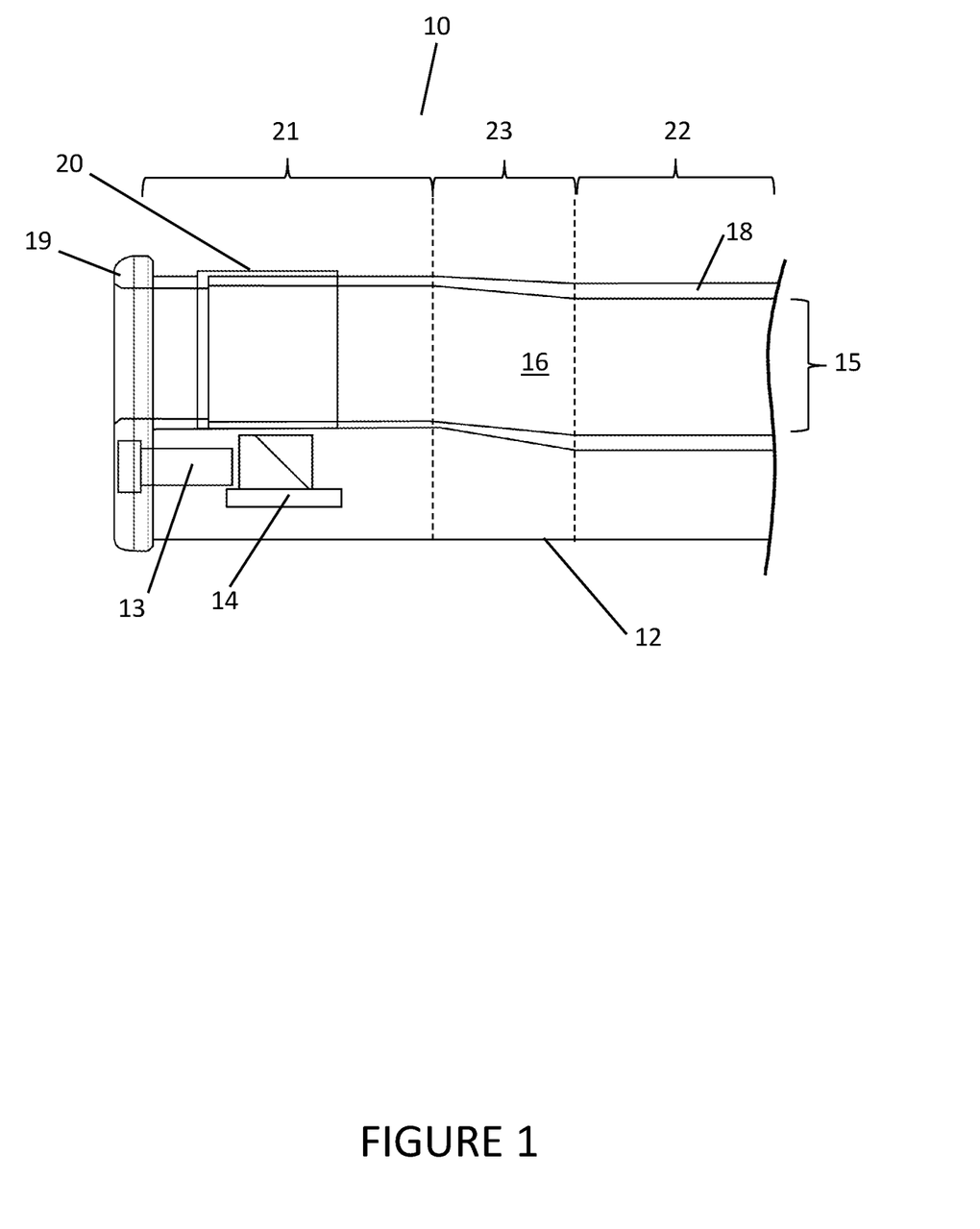
FIG. 1 shows a simplified, open view of an endoscope device.

FIG. 1 shows a simplified schematic, open view of an endoscope device 10 of an endoscope, seen in a side view of the distal end region of the device. In the shown implementation, the endoscope is a flexible endoscope. Alternatively, however, the endoscope could also be a rigid endoscope. Parts of the endoscope shaft 12 are not shown in the figure, so as to provide a clearer view of the components in the interior.

In the shown embodiment, the endoscope device 10 forms a part of the endoscope. It could also form the entire endoscope. The endoscope device 10 has an endoscope shaft 12. Further components of the endoscope device 10 useful in the field of endoscopy, such as an irrigation channel, optical waveguide or the like, may be arranged in the endoscope shaft 12. For the sake of clarity, these further components are not shown. In the figure, an optical unit 13 and an image sensor 14 are shown inside a distal region (on the left in the figure) of the endoscope shaft 12.

The endoscope device 10 has a working channel 15. The working channel 15 is arranged in the endoscope shaft 12. The working channel 15 has a working channel volume 16. The working channel 15 has a working channel sheath 18. The working channel sheath 18 encloses the working channel volume 16. The working channel sheath 18 has a constant internal diameter along a principal extent of the working channel. In this way, at least one surgical instrument can be arranged in the working channel volume 16 in an operating state. The working channel 15 moreover extends at a slight angle from the proximal end (on the right in the figure) to the distal end.

For the arrangement of the components of the endoscope device 10, the endoscope device 10 has a distal endoscope tip 19. For this purpose, the endoscope tip 19 has a working channel receptacle 20, in which a distal end portion of the working channel 15 can be arranged. The working channel 15 is connected to the endoscope tip 19 by cohesive bonding, usually by gluing. Alternatively, however, the working channel 15 could also be connected to the endoscope tip 19 by force-fit and/or form-fit engagement.

For arrangement of the working channel 15 at the endoscope tip 19, the working channel sheath 18 has a variable external diameter along the principal extent of the working channel 15. The working channel sheath 18 has a distal, or further, portion 21. In the present case, the working channel sheath 18 tapers in regions along the distal direction. That is, the external diameter decreases in portions in the distal direction, while the internal diameter, preferably, remains constant.

The working channel sheath 18 has a proximal, or first, portion 22. In the proximal portion 22, the external diameter of the working channel sheath 18 is constant along the principal extent of the working channel 15. Moreover, the working channel sheath 18 has a distal portion 21. In the present case, the distal portion 21 is a distal end portion of the working channel 15. In the proximal portion 22, the external diameter is constant along the principal extent of the working channel 15. A wall thickness of the working channel sheath 18 in the proximal portion 22 is constant along the principal extent of the working channel. The external diameter of the working channel sheath 18 in the distal portion 21 is at least 10% smaller than the external diameter in the proximal portion 22. A wall thickness of the working channel sheath 18 in the distal portion 21 is constant along the principal extent of the working channel. The wall thickness in the distal portion is at least 10% smaller than the wall thickness in the proximal portion 22. Moreover, the working channel sheath 18 has a middle, or in-between, portion 23. The middle portion 23 is arranged between the distal portion 21 and the proximal portion 22. In the middle portion 23, the external diameter of the working channel sheath 18 decreases continuously along the principal extent of the working channel 15. In the middle portion 23, the external diameter of the proximal portion 22 merges continuously into the external diameter of the distal portion 21. In the middle portion 23, the wall thickness of the working channel sheath 18 decreases continuously along the principal extent of the working channel 15. In the middle portion 23, the wall thickness of the proximal portion 22 merges continuously into the wall thickness of the distal portion 21.

Figure 2:
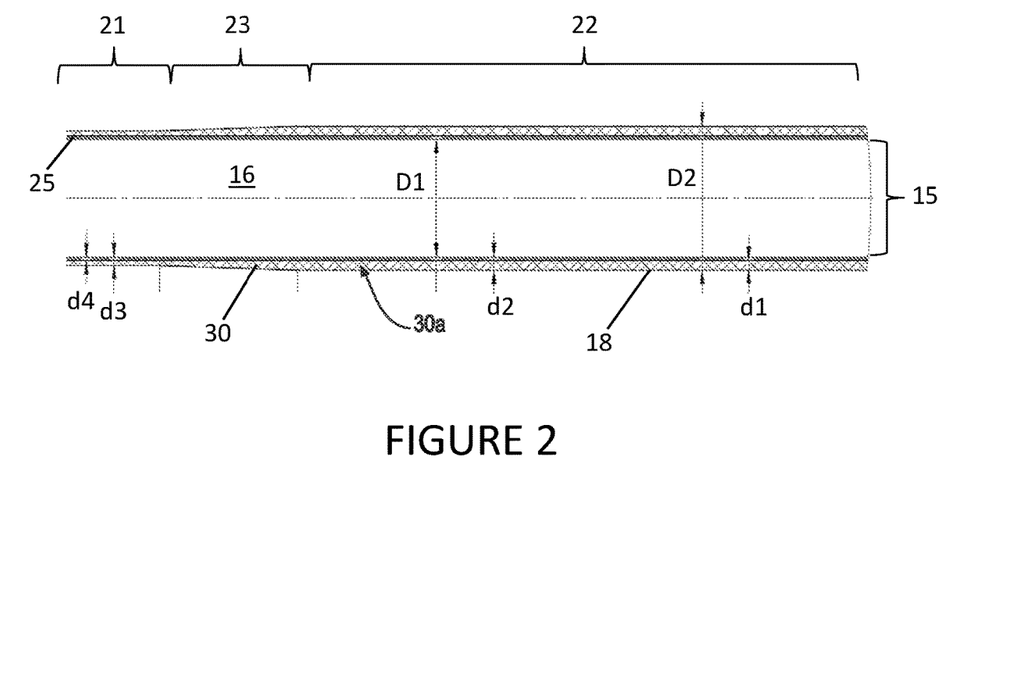
FIG. 2 shows detail of a working channel of an endoscope device.

The details of the working channel sheath 18 are shown in the embodiment shown in FIG. 2. The figure shows a distal detail of the working channel 15, as has been described with reference to FIG. 1, wherein the channel 15 here extends, without being angled, with a constant internal diameter from the proximal end to the distal end (from right to left in the figure). The working channel sheath 18 has at least a first sheath layer 25. The first sheath layer 25 forms an inner face of the working channel sheath 18. The first sheath layer 25 comprises at least one plastic material. In the shown embodiment, the first sheath layer 25 comprises only one plastic material. In other words, the plastic material forms the first sheath layer 25 entirely. In the present case, the plastic material is polytetra-fluoroethylene (P T F E). Alternatively, the plastic material could also be another thermally stable plastic that withstands an autoclaving process. The plastic material of the sheath layer 25 is free of pores 30a (FIG. 2). The plastic material has a density of less than 3 g/cm³. Moreover, the plastic material has a density of at most 2.4 g/cm³. In the present case, the plastic material has a density of 2.2 g/cm³.

Figure 3:
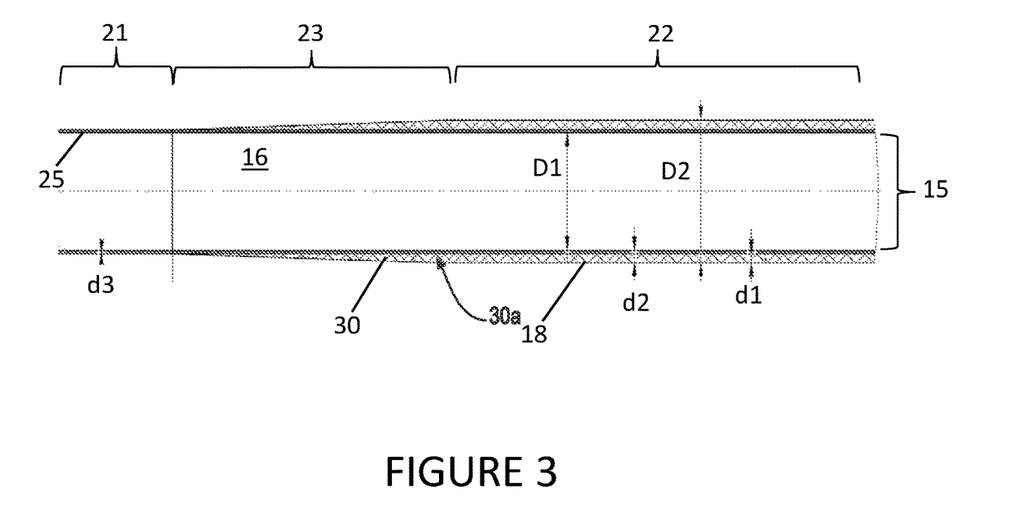
FIG. 3 shows detail of an alternative embodiment of a working channel of an endoscope device.

In FIGS. 2 and 3, the diameters and different thicknesses are indicated by arrows. D1 designates the internal diameter of the working channel sheath 18, D2 designates the external diameter of the working channel sheath 18, d1 designates the thickness of the further sheath layer 30 in a proximal region, d2 designates the thickness of the sheath 18 in a proximal region 22, d3 designates the thickness of the further sheath layer 30 in a distal region 21, and d4 designates the thickness of the first sheath layer 25. The further reference signs designate the same parts as have already been explained with reference to FIG. 1.

The first sheath layer 25 has a layer thickness d4. The layer thickness d4 of the first sheath layer 25 corresponds to at least 2% of the internal diameter D1 of the working channel sheath 18. The layer thickness d4 is constant along the principal extent of the working channel 15. The direction of the principal extent is indicated in FIG. 3 by a broken line along the working channel 15. The layer thickness d4 of the first sheath layer has the same value in the different portions 21, 22 and 23 of the working channel 15.

The working channel sheath 18 has at least one further sheath layer 30. The further sheath layer 30 forms an outer face of the working channel sheath 18. The sheath layer 25 and the further sheath layer 30 lie on each other. The sheath layer 25 and the further sheath layer 30 are connected to each other by cohesive bonding. Alternatively, or in addition, the sheath layer 25 and the further sheath layer 30 could also be connected to each other by form-fit engagement.

The further sheath layer 30 comprises at least one further plastic material. In the present case, the further sheath layer 30 comprises only one plastic material. In other words, the further plastic material forms the further sheath layer 30 entirely. The further plastic material is different than the plastic material of the sheath layer 25. In the present case, the further plastic material is expanded polytetrafluoroethylene (ePTFE). Alternatively, the plastic material could also be another thermally stable expanded plastic that withstands an autoclaving process. On account of the expansion process in its production, the further plastic material of the further sheath layer 30 has pores 30a. The further plastic material has a density of at most 1.9 g/cm$^3$. Moreover, the plastic material has a density of at least 0.6 g/cm$^3$. In the present case, the plastic material has a density of 1.6 g/cm$^3$, wherein the density can be higher in a portion of lesser thickness d3 of the sheath layer 30, for example if the material has been compressed.

The further sheath layer 30 has a further layer thickness d1, d3. The further layer thickness d1, d3 is variable along the principal extent of the working channel 15. The layer thickness d1, d3 of the further sheath layer 30 decreases in portions along the principal extent of the working channel 15. In the present case, the layer thickness d1, d3 of the further sheath layer decreases in portions in the distal direction along the principal extent of the working channel 15.

In the proximal portion 22, the further sheath layer 30 has a layer thickness d1. This layer thickness d1 corresponds here to approximately 10% of the internal diameter D1 of the working channel 15. In the middle portion 23, the layer thickness of the further sheath layer 30 decreases continuously. In the present case, the layer thickness in the middle portion 23 decreases to the value d3, which corresponds to approximately half the thickness d1.

The wall thickness d2 consists of the sum of the layer thickness d4 of the sheath layer 25 and the further layer thickness d2 of the further sheath layer 30.

FIG. 3 shows a further embodiment of the invention. Here, the same reference signs also designate parts similar to those in FIGS. 1 and 2. The embodiment of the working channel 15 of the endoscope device 10 differs from the one in FIG. 2 in that a distal portion 21 of the working channel sheath 18 is free of the further sheath layer 30. The further dimensions and properties of the channel sheath 18 and of the sheath layers 25 and 30 are as described above. However, in a middle portion 23 of the sheath 18, the layer thickness of the further sheath layer 30 here decreases along the principal extent of the channel 15 from a value d1 not equal to zero in the proximal region 22 to a value d3 equal to zero or almost zero in the distal portion 21. The distal portion 21 can thus be free of the further sheath layer 30, and the sheath 18 is here formed only by the sheath layer 25.

Figure 4:
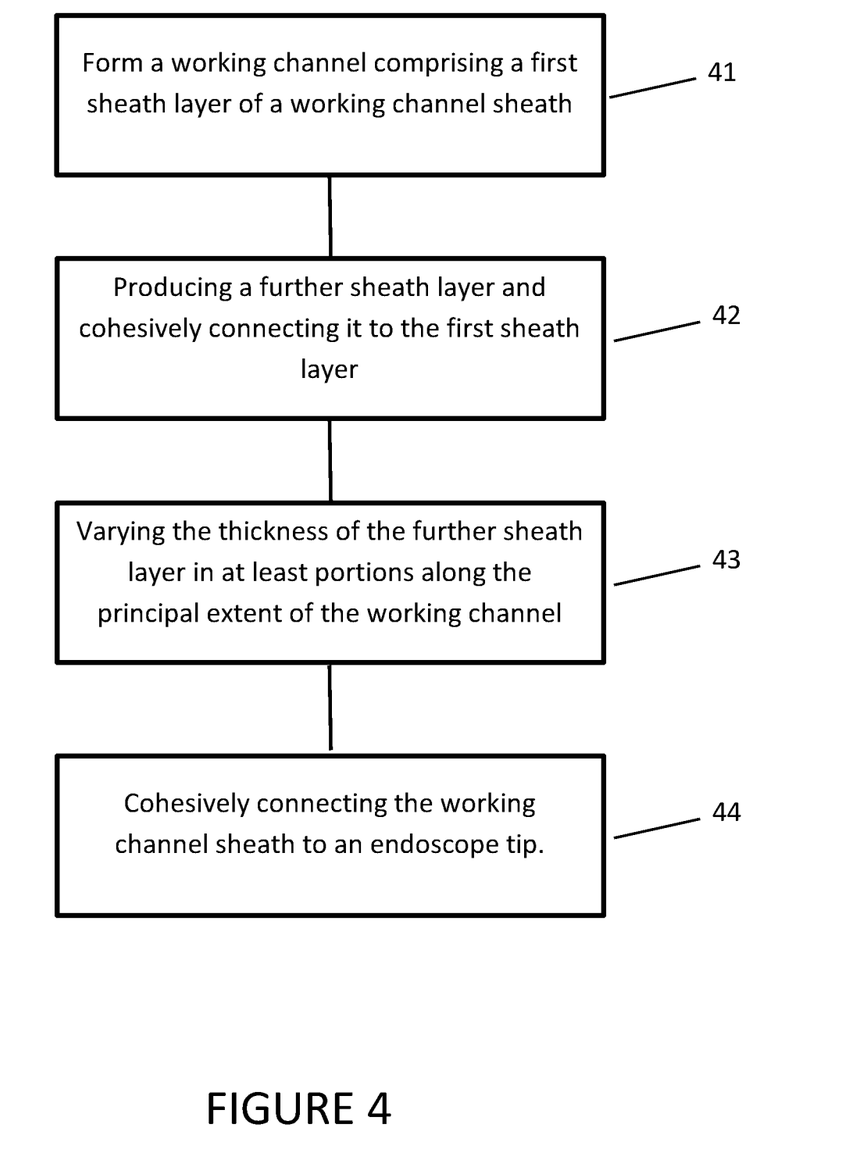
FIG. 4 shows the steps of a method for producing an endoscope device.

FIG. 4 shows a schematic flowchart of an example of a method for producing an endoscope device described above.

The method comprises forming a working channel 15, wherein a first sheath layer 25 of the working channel sheath 18 is produced by extrusion of the plastic material or by another method. A further sheath layer 30 of the working channel sheath 18 is produced in step 42. Moreover, the further sheath layer 30 is cohesively connected to the first sheath layer 25. For this purpose, the further plastic material is applied to the sheath layer 25 and then expanded by heat.

In method step 43, the thickness of the further sheath layer 30 is varied at least in portions along the principal extent of the working channel 15. For this purpose, the further sheath layer 30 is heated in said portion and subjected to pressure. In this way, the further plastic of the further sheath layer 30 is compacted and thus at least partially converted into the plastic of the sheath layer 25. For this purpose, the working channel sheath 18 can be inserted into a funnel, which tapers to a point, until the latter comes into contact with the working channel sheath 18. In order to vary the further sheath layer 30 or the layer thickness thereof, in particular in order to reduce or remove same, it is possible for example to use a turning method or also an etching method.

Method step 44 comprises cohesively connecting the working channel sheath 18 to the endoscope tip 19. For this purpose, an adhesive is applied to the working channel sheath 18, and the working channel sheath 18 is inserted into the working channel receptacle 20 of the endoscope tip 19.

The method can comprise further steps for improving the working channel and the endoscope device.

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. An endoscopic device have a tip comprising:
    a tubular working channel sheath inserted into the tip, the tubular working channel sheath including a working channel, a first sheath layer and a second sheath layer;
    wherein the working channel includes a proximal portion, a distal portion, and an intermediate portion interposed between the proximal portion and the distal portion;

the first sheath layer bounds and is concentric to the working channel and includes at least one plastic material, the first sheath layer having a constant layer thickness along an entire length of the working channel, the first sheath layer formed of a first plastic material that is nonporous; and wherein the second sheath layer bounds and is concentric to the first sheath, the second sheath layer including at least one second plastic material different than the first plastic material of the first sheath layer, the second sheath layer having a tapered layer thickness along a length of the working channel, wherein the tapered layer thickness tapers constantly along the intermediate portion of the working channel wherein a length of the proximal portion is greater than a length of the intermediate portion, and a length of the intermediate portion is greater than a length of the distal portion, and the second plastic material is free of pores along the intermediate portion and includes pores along the proximal portion of the second sheath layer.

2. The endoscopic device of claim 1, further comprising a distal portion, a proximal portion, and an intermediate portion defined therebetween, wherein the second sheath layer has a constant thickness along the proximal portion.

3. The endoscopic device of claim 2, wherein the tapered layer thickness is defined between the proximal portion and the distal portion.

4. The endoscopic device of claim 2, wherein the distal portion is free of the second sheath layer.

5. The endoscopic device of claim 2, further comprising:
an internal diameter constant along the length of the working channel; and
an external diameter, wherein the external diameter at the proximal portion is greater than the external diameter at the distal portion.

6. The endoscopic device of claim 5, wherein the external diameter of the proximal portion is converged with the external diameter of the distal portion at the intermediate portion.

7. The endoscopic device of claim 5, wherein a thickness of the first sheath layer is at least 2 percent of the internal diameter.

8. The endoscopic device of claim 7, wherein a thickness of the second sheath layer is at least 10 percent of the internal diameter at the proximal portion.

9. The endoscopic device of claim 2, wherein the constant thickness of the second sheath layer has a density less than a density of the first sheath layer.

10. The endoscopic device of claim 1, wherein the second sheath layer is coupled to the first sheath layer via form-fit engagement.

11. The endoscopic device of claim 1.

12. The endoscopic device of claim 1, wherein the first plastic material of the first sheath layer has a density of up to approximately 2.4 g/cm$^3$.

13. The endoscopic device of claim 1, wherein at least one of the plastic materials is polytetrafluoroethylene (PTFE).

14. The endoscopic device of claim 1, wherein an axis of the intermediate portion is angled relative to an axis of the proximal portion and an axis of the distal portion, and wherein the axis of the proximal portion is parallel to the axis of the distal portion.

15. An endoscopic device have a tip, comprising:
a working channel sheath inserted into the tip, the working channel sheath including a working channel, a first sheath layer and a second sheath layer; and wherein
the first sheath layer includes at least one plastic material, the first sheath layer having a constant layer thickness along an entire length of a proximal portion, a distal portion, and an intermediate portion therebetween of the working channel, the first sheath layer formed of a first plastic material that is nonporous; and wherein
the second sheath layer bounding and concentric to the first sheath layer, the second sheath layer includes at least one further plastic material different than the plastic material of the first sheath layer, the second sheath layer having a layer thickness that tapers along a length of the working channel, wherein the layer thickness of the second sheath layer tapers along the intermediate portion of the working channel sheath, the layer thickness of the second sheath layer is constant along the proximal portion, and the thickness layer along the intermediate portion tapers to zero so as to expose the first sheath layer along the distal portion, and the second plastic material is free of pores along the intermediate portion and includes pores along the proximal portion of the second sheath layer.

16. The endoscopic device of claim 15, wherein the layer thickness of the second sheath layer decreases from the intermediate portion to the distal portion.

17. The endoscopic device of claim 15, wherein a length of the distal portion is greater than a length of the intermediate portion, and a length of the intermediate portion is greater than a length of the distal portion.

18. The endoscopic device of claim 15, wherein an axis of the intermediate portion is angled relative to an axis of the proximal portion and an axis of the distal portion, and wherein the axis of the proximal portion is parallel to the axis of the distal portion.

19. A method for producing an endoscope device for a flexible endoscope comprising the steps of:
forming a working channel, with a tubular working channel sheath that encloses a working channel volume of the working channel, the working channel includes a proximal portion, a distal portion, and an intermediate portion interposed between the proximal portion and the distal portion, the tubular working channel sheath includes a first sheath layer and a second sheath layer, the first sheath layer includes a first plastic material, and the second sheath layer bounds and is concentric to the first sheath layer, the second sheath layer includes a second plastic material, the first plastic material different than the second plastic material, the first plastic material being nonporous;
maintaining a constant layer thickness of the first sheath layer along a length of the working channel;
constantly tapering a layer thickness of the second sheath layer along the length of intermediate portion of the working channel, wherein a length of the proximal portion is greater than a length of the intermediate portion, and a length of the intermediate portion is greater than a length of the distal portion and the second plastic material is free of pores along the intermediate portion and includes pores along the proximal portion of the second sheath layer; and
cohesively connecting the working channel to an endoscope tip.

20. The method of claim 19, wherein an axis of the intermediate portion is angled relative to an axis of the proximal portion and an axis of the distal portion, and wherein the axis of the proximal portion is parallel to the axis of the distal portion.

* * * * *